United States Patent
Nawata et al.

(10) Patent No.: US 10,345,224 B2
(45) Date of Patent: Jul. 9, 2019

(54) OPTICAL RESPONSE MEASURING DEVICE AND OPTICAL RESPONSE MEASURING METHOD

(71) Applicant: RIKEN, Saitama (JP)

(72) Inventors: Kouji Nawata, Saitama (JP); Hiroaki Minamide, Saitama (JP); Shuzhen Fan, Saitama (JP); Feng Qi, Saitama (JP); Hiromasa Ito, Saitama (JP)

(73) Assignee: RIKEN, Saitama (JP)

( * ) Notice: Subject to any disclaimer, the term of this patent is extended or adjusted under 35 U.S.C. 154(b) by 156 days.

(21) Appl. No.: 15/517,925

(22) PCT Filed: Oct. 5, 2015

(86) PCT No.: PCT/JP2015/078254
§ 371 (c)(1),
(2) Date: Apr. 7, 2017

(87) PCT Pub. No.: WO2016/056522
PCT Pub. Date: Apr. 14, 2016

(65) Prior Publication Data
US 2017/0307515 A1    Oct. 26, 2017

(30) Foreign Application Priority Data
Oct. 8, 2014 (JP) .................... 2014-207559

(51) Int. Cl.
*G01N 21/17* (2006.01)
*G01N 21/3581* (2014.01)
(Continued)

(52) U.S. Cl.
CPC ......... *G01N 21/17* (2013.01); *G01N 21/3581* (2013.01); *G02F 1/365* (2013.01); *G02F 1/37* (2013.01); *G02F 2001/354* (2013.01)

(58) Field of Classification Search
CPC .... G01N 21/17; G01N 21/3581; G02F 1/365; G02F 1/37; G02F 2001/354
See application file for complete search history.

(56) References Cited

U.S. PATENT DOCUMENTS

| | | | |
|---|---|---|---|
| 5,321,501 A | 6/1994 | Swanson et al. | |
| 5,451,785 A * | 9/1995 | Faris | A61B 5/0086 250/330 |

(Continued)

FOREIGN PATENT DOCUMENTS

| | | |
|---|---|---|
| JP | 4-174345 A | 6/1992 |
| JP | 2004-317573 A | 11/2004 |

(Continued)

OTHER PUBLICATIONS

Crawley et al., "Area-scan camera for terahertz holography," *Rev. Sci. Instrum.* 77:053106, 2006. (4 pages).

(Continued)

*Primary Examiner* — Michael A Lyons
(74) *Attorney, Agent, or Firm* — Seed IP Law Group LLP

(57) ABSTRACT

An optical response measuring device is provided with a light source, first and second wavelength conversion elements and a light intensity sensor array. The light source generates a pair of light beams including light beams of first and second wavelengths, and the first wavelength conversion element generates measurement light. The measurement light is irradiated on an object for measurement and a detection light having first phase and second phase is obtained in response to this irradiation. A reference light that carries the phase of the pair of the pair light beams and the detection light both pass through a second wavelength conversion element to obtain a modulated reference light (Continued)

have first and second intensities. The first and second local intensities are then measured by the light intensity sensor array.

8 Claims, 6 Drawing Sheets

(51) Int. Cl.
*G02F 1/37* (2006.01)
*G02F 1/365* (2006.01)
*G02F 1/35* (2006.01)

(56) References Cited

U.S. PATENT DOCUMENTS

| | | | |
|---|---|---|---|
| 5,956,355 A | 9/1999 | Swanson et al. | |
| 8,735,823 B2 | 5/2014 | Ouchi | |
| 2006/0268945 A1 | 11/2006 | Minamide et al. | |
| 2010/0271618 A1* | 10/2010 | Ito | G01N 21/3581 356/51 |
| 2011/0058155 A1* | 3/2011 | Ohno | G01N 21/3581 356/51 |
| 2014/0061474 A1* | 3/2014 | Kitamura | G01J 3/42 250/339.02 |
| 2014/0191131 A1* | 7/2014 | Uchida | G02F 1/3544 250/341.8 |

FOREIGN PATENT DOCUMENTS

| | | |
|---|---|---|
| JP | 2005-172779 A | 6/2005 |
| JP | 2010-156674 A | 7/2010 |
| WO | 92/19930 A1 | 11/1992 |
| WO | 2006/085403 A1 | 8/2006 |

OTHER PUBLICATIONS

Extended European Search Report, dated Feb. 28, 2018, for European Application No. 15848227.3-1022, 9 pages.
International Search Report from PCT/JP2015/078254 dated Dec. 8, 2015.

\* cited by examiner

OPTICAL RESPONSE MEASURING DEVICE AND OPTICAL RESPONSE MEASURING METHOD

BACKGROUND

Technical Field

The present invention relates to an optical response measuring device and optical response measuring method. More specifically, the present invention relates to an optical response measuring device and optical response measuring method that are capable of capturing tomograms by way of light, or electromagnetic waves, without requiring optical scanning operation as a prerequisite.

Description of the Related Art

Optical coherence tomography (OCT) utilizing light, or an electromagnetic wave, has been developed recently for one of non-destructive and non-invasive methodologies in order for conducting tomography on an observation object. The OCT has been applied to obtain tomograms of, for example, retina on fundus oculi or an endothelial wall of a blood vessel to date, and it is currently applied even to clinical applications. The OCT adopts coherent light of a wavelength in a near infrared range, as an example, for light beam irradiated to an object for measurement, or measurement light. Based on difference observed in an optical response from a structure of substance or tissues ("feature under measurement") under illumination of light for detection, or detection light in comparison with its surroundings, position of each structural detail inside the feature under measurement is calculated the OCT, and imaging is then conducted if needed. The OCT adopts an optical configuration of that of Michelson interferometer. To be more specific, one of two optical paths of the Michelson interferometer, or arms, is used for light to be impinged upon a reference mirror, which is used as reference light; whereas the other of the arms is used for light to be incident into an object for measurement, which is used as measurement light. The structural information along a depth direction, or an invasive direction, is obtained while the measurement light is irradiated to the object for measurement. What is extracted from the object for measurement is reflected or back-scattered light, or detection light, which is then made to travel along the same optical path again for correlation or for making an interference with the reference light for allowing an intensity measurement. Since the OCT can produce high resolution images, it has been expected to be a tool for carrying out a biopsy with non-destructive and non-invasive capabilities.

OCT technology of an early date, or time domain OCT (TD-OCT) needed a scan operation for changing an optical path length for reference light in a mechanical way (see for example, Patent Documents 1 and 2). Instead of the mechanical scanning of the optical path length, a plurality of wavelengths is used in recent OCT technology for obtaining structural information in an invasive direction of light for capturing higher resolution images or for imaging in a real time manner, or the like. The type of OCTs that use light of a plurality of wavelengths is called a Fourier domain OCT (FD-OCT), as it adopts Fourier transform in some way. The FD-OCTs are broadly classified into two types: one for spectral domain OCTs, or SD-OCTs, in which measurement light of multiple wavelengths are irradiated at a time for deriving spectral information through spectrometry (see for example Patent Document 3), and the other for swept-source OCTs, or SS-OCTs, in which frequency is swept for obtaining spectral information from intensity signal at each frequency value, though mere a single frequency or wavelength light is used at every moment (see for example Patent Document 3). In the FD-OCTs including these types, coherent light such as laser light is irradiated and optical intensity to an object for measurement and a light intensity is measured by using interferometry, where the light intensity is responsive to phase of the response light, or detection light, returning back from the object for measurement.

RELATED ART REFERENCES

Patent Documents

[Patent Document 1] JP 1992-174345 A
[Patent Document 2] JP 1994-511312 T (U.S. Pat. No. 5,321,501 B)
[Patent Document 3] U.S. Pat. No. 5,956,355 B
[Patent Document 4] JP 2004-317573 A (Japanese Patent No. 4183546 B)

Technical Problem

It is necessary to adopt scan optics, such as a galvanometer mirror, when conducting image formation in existing OCTs. This is because information that can be gathered from phase information for obtaining information along a depth direction (invasion direction) in existing OCTs is limited to information at a single point under illumination and information at each position along a depth direction (invasion direction) behind the point under illumination. That is, in order to obtain a tomogram from an illuminated area on the object for measurement, it is necessary to obtain information along a ray of the measurement light at a single point under illumination along at least a single line for the information extending along an invasive direction of the point under illumination. The information along the invasive direction at a single point under illumination can be obtained by scanning action that actually changes optical path length in a mechanical way for the TD-OCT, by spectrometry (for SD-OCT) or by frequency sweeping (for SS-OCT) in the case of FD-OCT. The operation of the information capturing along an invasive direction of light at each point under illumination of such types is called "A-scan". In the case of the FD-OCT, it is not necessary to carry out mechanical scanning in the A-scan. However, when it comes to obtaining a tomogram, it is still necessary to conduct scanning operation that shifts point under illumination along a line in a consecutive manner even for the FD-OCTs. The operation of this sort for obtaining a tomogram is called "B-scan" for which mechanical scanning optics such as a galvanometric mirror is required in the FD-OCTs. Moreover, when it comes to obtaining a volume image or voxel data over the three-dimensional volume range, it will be necessary to additionally conduct scanning operation in another direction along which the scan line itself in the illumination area is shifted. As stated above, the existing OCTs still require mechanical scanning operation on a line or concerning a two-dimensional range for a tomogram, or a volume image over the three-dimension, even other than the TD-OCTs. Consequently, the number of images captured per a unit time is limited in the existing OCTs. For improving measurement rate of at points under illumination that are conducted in a consequent manner in the existing OCTs, improving frequency sweep rate has been a target especially in SS-OCT.

On top of that, since the detection light obtained by irradiating the measurement light and the reference light has an identical wavelength, it is necessary for the intensity measurement in the existing OCTs to adopt detectors that show sensitivity at this wavelength. For the SD-OCTs, a polychromator of a spectrometer having a dispersion element, such as a diffractometer, combined with a one-dimensional sensor array is adopted. However, only limited materials can be used for the sensor array due to restrictions in integrated circuit technology; therefore, a wavelength range that gives sensitivity for detection is also limited. In addition to that, although the SS-OCTs do not require a sensor array, only photo detectors with high speed response capability can be used for the SS-OCTs. In fact, only a limited wavelength range can be furnished with such kind of photo detectors. From the circumstances mentioned above, practicality is found in the OCTs only when wavelength ranges are adopted where appropriate detectors are available. It is imperative to account for the restrictions on the photo detectors when choosing a wavelength to be used for the measurement light in accordance with optical properties of the object for measurement.

BRIEF SUMMARY

It is therefore necessary to provide a solution in the present invention for at least some of the problems mentioned above.

The present invention summary contributes to development of technology for capturing a tomogram based on the optical wave, by enabling more unrestricted selection of wavelength of light for the measurement.

The inventors concentrated on the detection process, namely the receiving process of light, which not been improved in existing OCTs. Among others, they made use of non-linear wavelength conversion for the detection processes. They realized that certain measurements can be obtained without conducting a scanning operation. In the case when coherent light, such as laser light, is made incident into media that shows non-linearity in response to an optical electric-field, deviation away from linear response of electrons in the media become significant as the optical electric-field is strengthened, which will be observed as non-linear optical phenomenon. If we adopt such a non-linear optical phenomenon, a wavelength of input light can be converted into another wavelength. In addition to that, we noted that in the non-linear optical phenomenon, related phenomenon, such as wavelength conversion, should be sensitive to phase of light, or detection light, obtained from an object for measurement. If such a property is applied to processing of the detection or receiving process of light, then it should be possible to detect phase information even when wavelength of light is more freely selected for the measurement light or the detection light.

That is, in one aspect of the present invention provided is an optical response measuring device for an object for measurement comprising: a light source for generating a pair of light beams having light beams of a first wavelength and a second wavelength; a first wavelength conversion element, on which the pair of light beams is made incident, for generating measurement light of a measurement wavelength whose phase is maintained with relative to the pair of light beams incident thereon; a second wavelength conversion element, on which a detection light obtained from an illuminated area on an object for measurement irradiated by the measurement light is made incident, for generating modulated reference light when both of reference light and light whose phase needs to be determined are made incident thereon, wherein the reference light carries the phase of the pair of light beams, wherein the light whose phase needs to be determined is included in the detection light, wherein the detection light has a first phase and a second phase that are influenced by responses of the object for measurement to the measurement light at a first point under illumination and a second point under illumination in the illuminated area, and wherein the modulated reference light are modulated to have a first local intensity and a second local intensity in accordance respectively with the first phase and the second phase of the detection light; and a light intensity sensor array, on which the modulated reference light is made incident, for measuring the first local intensity and the second local intensity of the modulated reference light that correspond respectively to the first phase and the second phase of the detection light.

The aspect mentioned above can also be practiced as a process. That is, in another aspect of the present invention provided is an optical response measuring method of an object for measurement comprising the steps of: generating a pair of light beams having light beams of a first wavelength and a second wavelength; obtaining measurement light of a measurement wavelength whose phase is maintained with relative to the pair of light beams by making the pair of light beams incident on a first wavelength conversion element; obtaining detection light having a first phase and a second phase that are influenced by responses at a first point under illumination and a second point under illumination in an illumination area of an object for measurement by irradiating the measurement light to the illumination area; obtaining modulated reference light by making both of reference light carrying a phase of the pair of light beams and the detection light incident on a second wavelength conversion element for processing light whose phase needs to be determined in the detection light and the reference light through the second wavelength conversion element, wherein the modulated reference light are modulated to have a first local intensity and a second local intensity in accordance with the first phase and the second phase in the detection light; and measuring the first local intensity and the second local intensity in the modulated reference light that correspond respectively to the first phase and the second phase in the detection light by making the modulated reference light incident on a light intensity sensor array.

In the aspects of the present invention mentioned above, it is preferable to adopt a collinear phase matching condition for matching the phase in the non-linear wavelength conversion. That is, in the above-mentioned aspects of the present invention provided is the optical response measuring device, or the optical response measuring method, for an object for measurement, wherein the light whose phase needs to be determined in the detection light and the reference light are made incident on the second wavelength conversion element while being aligned with each other, and wherein the modulated reference light is generated under a collinear phase matching condition.

Furthermore, in addition to those mentioned above, as yet another aspect of the present invention, a device having similar functionality can be provided when a light source of a single wavelength and a wavelength conversion element are adopted, where the wavelength conversion element generates light of plural wavelengths from output of the light source. That is, in yet another aspect of the present invention provided is an optical response measuring device for an object for measurement comprising: a light source for generating a light beam of a first wavelength; a first wavelength conversion element, on which the light beam of the first wavelength is made incident, for generating measurement light of a measurement wavelength and a light beam of a second wavelength; a second wavelength conversion element, on which a detection light obtained from an illuminated area on an object for measurement irradiated by the measurement light is made incident, for generating modulated reference light when both of reference light and the detection light are made incident thereon, wherein the reference light carries the phases of the light beams of the first and second wavelengths, wherein the detection light has a first phase and a second phase that are influenced by responses of the object for measurement to the measurement light at a first point under illumination and a second point under illumination in the illuminated area, and wherein the modulated reference light are modulated to have a first local intensity and a second local intensity in accordance respectively with the first phase and the second phase of the detection light; and a light intensity sensor array, on which the modulated reference light is made incident, for measuring the first local intensity and the second local intensity of the modulated reference light that correspond respectively to the first phase and the second phase of the detection light.

The aspects of the present invention mentioned above can be reduced into practice in a process invention. That is in yet another aspect of the present invention provided is an optical response measuring method of an object for measurement comprising steps of: generating a light beam of a first wavelength; obtaining measurement light of a measurement wavelength and a light beam of a second wavelength, wherein the measurement light has a phase that is maintained with relative to the pair of light beams, by making the light beam of the first wavelength incident on a first wavelength conversion element; obtaining detection light having a first phase and a second phase that are influenced by responses at a first point under illumination and a second point under illumination in an illumination area of an object for measurement by irradiating the measurement light to the illumination area; obtaining modulated reference light by making both of reference light carrying phases of the light beams of the first and the second wavelengths incident on a second wavelength conversion element for processing light whose phase needs to be determined in the detection light and the reference light through the second wavelength conversion element, wherein the modulated reference light are modulated to have a first local intensity and a second local intensity in accordance with the first phase and the second phase in the detection light; and measuring the first local intensity and the second local intensity in the modulated reference light that correspond respectively to the first phase and the second phase in the detection light by making the modulated reference light incident on a light intensity sensor array.

In the above-mentioned aspects of the present invention where a pair of light beams is adopted, a laser is utilized for a light source for the pair of light beams. Technique for generating the pair of light beams is not limited in the present invention. For example, it is possible to generate near infrared light having two wavelengths for the pair of light beams, from pump light or light of a single wavelength, such as an Nd:YAG laser, by using an optical parametric oscillation in KTiOPO$_4$ crystal, or KTP-OPO. It is to be noted that the optical parametric oscillator for generating the pair of light beams itself is also a wavelength conversion element, but it is different one of the first or the second wavelength conversion element in the aspects mentioned above. It is also preferable to adopt a fiber ring laser to which a chirp fiber Bragg grating and a semiconductor amplifier for lasing are used, or to adopt direct generation of the pair of the light beams in a laser that is capable of lasing operation at two wavelengths at a time in infrared range. Each light beams of each wavelength that makes the pair of light beams generated by such devices may have a significant coherence.

In aspects of the present invention that adopt light of a single wavelength, typical light sources include a fundamental wave (wavelength: 1064 nm), a second harmonics (wavelength: 532 nm), and a third harmonics (wavelength: 355 nm) of an Nd:YAG laser.

The expression of the first and the second wavelengths in any aspects of the present invention are used merely to distinguish wavelengths with each other when describing the pair of light beams or the wavelengths themselves; thus the values of the wavelengths, numerical ranges of the wavelengths when they are modulated, if needed, as well as an intensity ratio between them are suitably determined. These wavelengths decide the wavelength or the wavelength range of measurement light to be generated through a non-linear optical process at the first wavelength conversion element.

The first wavelength conversion element denotes an arbitrary element capable of converting wavelengths. Typical ones include a non-linear optical element of inorganic or organic crystal. The material of the crystal as well as its cutting plane is suitably selected for materials showing a non-linear response to an optical electric field due to symmetry of the crystal lattice or due to response of electrons of atoms or molecules in the crystal, in view of necessary property in the wavelength conversion, or in the frequency conversion. The wavelength conversion property can be observed when light of considerable intensity is processed through a material that show higher order non-linear susceptibility, such as a second order susceptibility ($\chi^{(2)}$) or a third order susceptibility ($\chi^{(3)}$). In the case the pair of light beams are adopted, the property of the non-linear wavelength conversion is any sort of properties, for which measurement light is generated from light of the first and the second wavelengths while keeping energy conservation process, such as difference frequency generation (DFG) or sum frequency generation that makes the measurement light to have a different frequency (or wavelength). Typical one for the first wavelength conversion element suitable for this aspect is one that performs the difference frequency generation.

On the other hand, in the aspect where the light of a single wavelength is adopted, any sort of properties for generating light of two different frequencies, or two different wavelengths, that satisfy energy conservation from the frequency corresponding to the first wavelength through optical parametric generation is used. An element that performs optical parametric generation (OPG) is one of typical and suitable for the first wavelength conversion element. In this aspect, the light of the two wavelengths to be generated include light of the second wavelength such as an idler light and the measurement light such as a signal light. The measurement light utilized in the aspects of the present invention is light that is generated by such non-linear wavelength conversion property.

As stated above, property of the first wavelength conversion element is to generate a pair of light beams from the light of the first and the second wavelengths, or to generate the measurement light from the light of the first wavelength.

Since the measurement light is an electromagnetic wave for detection to be irradiated to the object for measurement, it may include any sort of light of a wavelength that can be generated from light of the first and the second wavelengths, or from light of the first wavelength only. The wavelength of the measurement light, or measurement wavelength, may be selected according to purpose of measurement. Such selection may be made while several conditions are considered: whether the wavelength can be generated or not; and whether the desired wavelength conversion capability is possible in connection with the reference light by the second wavelength conversion element or not. On top of that, the wavelength is selected while considering relationship with the object for measurement.

Specifically, the wavelength of the measurement light irradiated to the object for measurement is chosen while considering whether the desired optical response is obtained or not. For example, in the application where an internal structure of the object for measurement is to be investigated, necessary amount of invasion (or transmission) is estimated and the wavelength is determined according to the application. A wavelength range where weak absorption by water is observed in the near infrared range may be suitable for obtaining a tomogram from inside of a living body, as an example. A THz wave may be suitable for examining internal structure of an object in a non-destructive manner because of its high transmittance, as another example. The measurement light maintains its phase with relative to the pair of light beams that has light of the first wavelength and light of the second wavelength. This will be described in detail later.

The object for measurement is any sort of physical body that is selected to be a target of the measurement in aspects of the present invention. It should be selected according to the purpose of the measurement. Various examples can be assumed for the object for measurement depending on the applications of the present invention. For example, surface or inner structure of any part of a living body selected for targets of OCTs may also be examined in an aspect of the present invention. Moreover, the wavelength for the measurement light may be selected from broader range than for OCTs. Thus, an object for measurement that could not be used in the OCTs may also be selected in the aspects of the present invention.

Illumination area may refer to an area having a two-dimensional area. It should be noted that the measurement light impinging on the illumination area may be transmitted into the inside of an object for measurement from the surface thereof in a depth direction (invasive direction) to create an illumination volume. Thus structural features along the invasive direction are obtained at each point of the illumination area at particular depth, or point under illumination. Typical illumination area for application of tomography for a three-dimensional structure has a two-dimensional area at different depths within the structure.

The first and the second points under illumination may include a point defined in the illumination area with a small area around the point and a volume range extending along the invasive direction of the measurement light from the point or the small area to a depth. For example, since the illumination area on the object for measurement is an area on which the measurement light is incident, the first and the second points under illumination are distinguishable points, or small areas represented by such points, on the surface of the object for measurement, (or at a selected depth) and volume includes those regions along the invasive direction of the measurement light within the illumination. The same applies for a third point under illumination in this application. The first-third points under illumination are mentioned for the purpose of describing the invention clearly.

Detection light is light to be detected and obtained from the object for measurement irradiated by the measurement light. The detection light has its own phase. This phase varies depending on the response of the object for measurement to the measurement light, as is the case for the phase in a usual electromagnetic wave. Such variations influence a delay from phase of the measurement light, or delay in phase or phase difference. In actual measurement, relative delay found in phase values in the detection light is transformed into intensity and then detected. The response of the object for measurement to the measurement light may include any type of response that leads to production of the detection light, including any of reflection, transmission, scattering (back, forward, or multiple scattering), diffusion, optical rotation, delay, birefringence, absorption, or depolarization, and so on, including any combination thereof. The factors that influence these responses are such structural features as material difference of the feature under measurement from the surroundings in the object for measurement, position of the feature under measurement in the object for measurement, and the like. Aside from the information of the phase, the detection light may convey information of the amplitude of optical electric-field, or intensity of light. The detection light is captured in a reverse direction of the measurement light, i.e., in a reflected direction from the object for measurement.

A second wavelength conversion element is also any sort of element that has a wavelength conversion capability similar to that of the first wavelength conversion element. The second wavelength conversion element may be of the same material of or of different material from the first wavelength conversion element. The second wavelength conversion element processes the reference light and the detection light irradiated thereto and thereby makes intensity of reference light be influenced by information conveyed by the detection light, such as intensity and phase. At this moment, the reference light irradiated to the second wavelength conversion element carries phase of the original pair of light beams. Typical reference light is a part of the light of the first wavelength, a part of the light of the second wavelength, or a part of both of them. Reference light that is irradiated to the second wavelength conversion element together with the detection light will have a modulated intensity according to the detection light. The modulation depth depends also on phase of the detection light. Reference light having modulation intensity by the second wavelength conversion element is called modulated reference light in this application.

Preferably, the second wavelength conversion element may be selected to be one that may work as stated above only when a collinear phase matching condition is satisfied with regard to light whose phase needs to be determined in the detection light.

The intensity of modulated reference light is measured by a light intensity detector. By adopting a light intensity sensor array having an array of plural optical intensity detectors for the light intensity detector, it will be possible to simultaneously determine each of plural local intensities (first and second local intensities) independently with each other in the modulated reference light. It follows that it is not always necessary to conduct focal point scanning or detection point scanning in determining the plural phases (first and second phases) in the detection light corresponding to the first and second points under illumination in the illumination area of the measurement light.

It should be noted that terminologies in this application are those that are customary used in the field of the present invention. For example, such expressions used in the field of optics as "light", "light source", "emission", "optical response", or "refraction" are adopted for electromagnetic waves or electromagnetic emissions that are not a part of the visible range, such as those in the infrared and terahertz ranges. For example, the term "terahertz light" denotes an electromagnetic wave in the terahertz range. Also, a single or plural images, or data for such images, may be expressed as "image." The image in such context may include a moving video image for duration of time.

Advantageous Effect of the Invention

According to any aspect of the present invention, it is possible to conduct measurement for obtaining tomograms while minimizing the need for scanning focal points as much as possible. Moreover, in any aspect of the present invention it is possible to choose a wavelength of light used in measurement with less restriction than before.

DETAILED DESCRIPTION

Embodiments regarding an optical response measuring device and a method for measuring optical response will be described. For all drawings, the common reference signs are given to common parts or elements unless otherwise noted.

Figure 1:
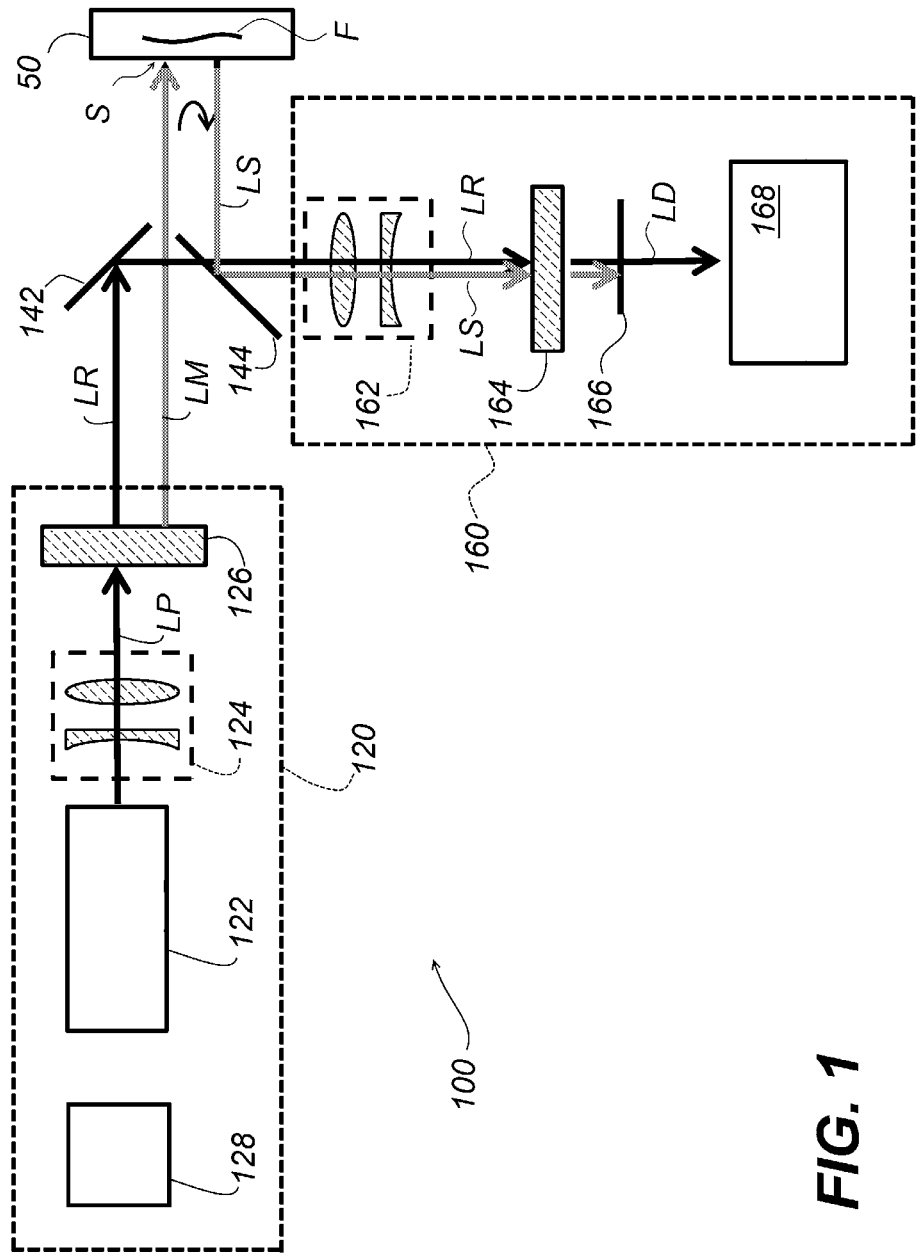
FIG. 1 is a schematic diagram illustrating an overall structure of an example optical response measuring device in an embodiment of the present invention.

1. Outline of Embodiment 1-1. When DFG (Difference Frequency Generation) Adopted
1-1-1. Overall Structure of Device
At first overall structure of an example device in the embodiment is outlined. For this purpose, a structure for generating the measurement light by using wavelength conversion by difference frequency generation (DFG) based on a pair of light beams is described. FIG. 1 is a schematic diagram illustrating an overall structure of an example optical response measuring device 100 in an embodiment of the present invention. The optical response measuring device 100 generally comprises illumination optics 120 for irradiating measurement light LM to an object for measurement 50 and detection optics 160 for receiving detection light LS obtained from the object for measurement 50 to which the measurement light is irradiated. The illumination optics 120 comprises light source 122 that generates light of two wavelengths (first and second wavelengths) and a wavelength conversion element (first wavelength conversion element 126). The detection optics 160 comprises another wavelength conversion element (second wavelength conversion element 164) and a sensor array (light intensity sensor array) 168. At least one set of telescope optics 124 and 162, or both of them, may be provided in at least one of the illumination optics 120 and detection optics 160, or both of them in cases where it is necessary to modify the arrangement for adjusting beam sizes, for example. Optical paths suitable for the measurement are arranged by providing a mirror 142 and a dielectric multi-layered mirror 144, if needed. A detection light cut filter 166 is also provided in the detection optics 160 if needed.

Figure 2:
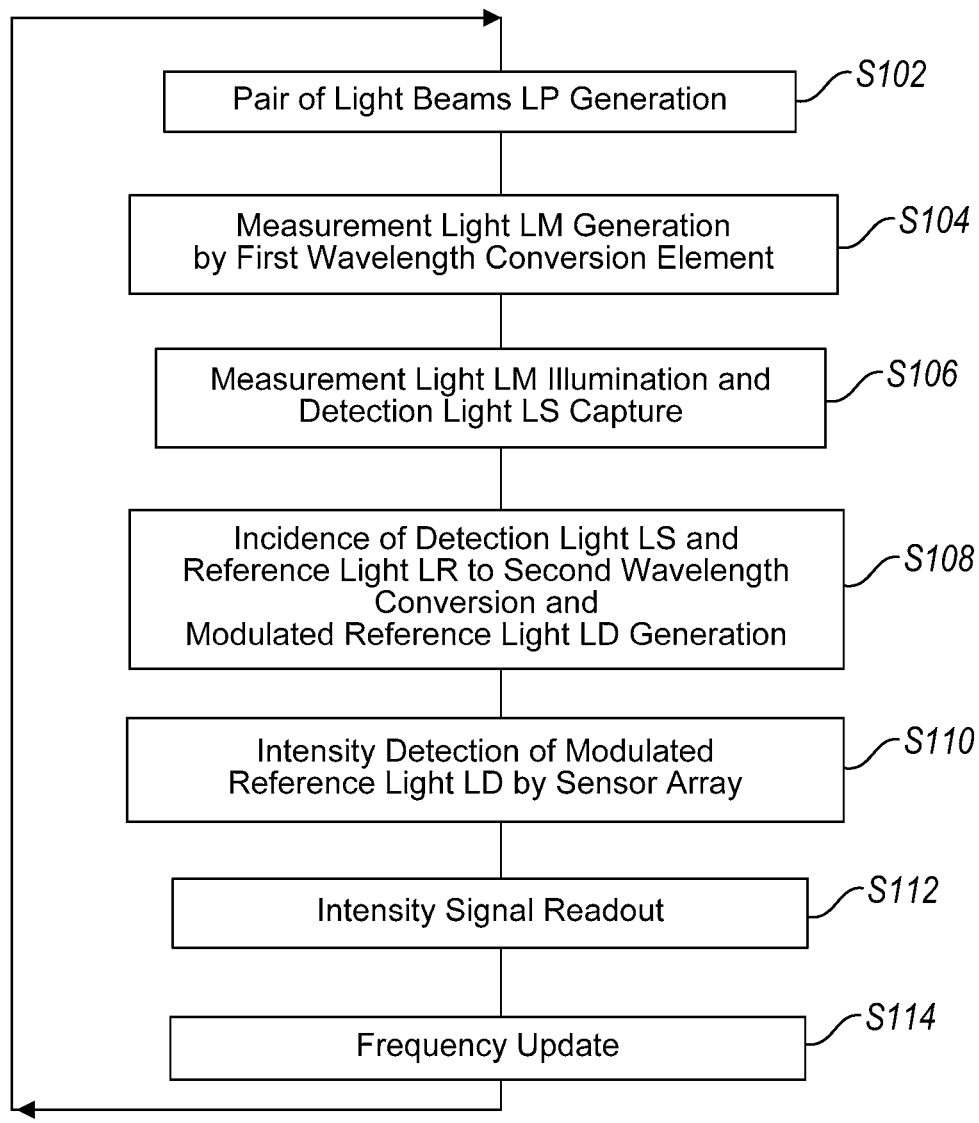
FIG. 2 is a flow chart indicating transition of states or operations in an example optical response measuring method that is embodied in an optical response measuring device of an embodiment of the present invention.

1-1-2. Phenomenon
Next described are physical phenomena when measurement is carried out by using the optical response measuring device 100 according to progress of time. FIG. 2 is a flow chart indicating transition of states or operations in an example optical response measuring method implemented into an optical response measuring device 100. The description will be made with reference also to FIG. 1. In the first place, the pair of light beams LP is generated (S102) at the light source 122. This pair of light beams LP is then irradiated to the first wavelength conversion element 126 for generating measurement light LM (S104). The measurement light LM is generated though non-linear wavelength conversion (for example, difference frequency generation) within the first wavelength conversion element 126. At this stage, light that carries the phase of the pair of light beams LP is used for reference light LR. The reference light LR is indicated in FIG. 1 by fraction of light of the pair of light beams LP that is transmitted through the first wavelength conversion element 126.

The measurement light LM is then irradiated to an object for measurement 50 for obtaining detection light LS, which represents optical response thereof (S106). At this stage, intensity and phase difference of detection light LS are determined according to the optical response at each point under illumination in the illumination area S of the object for measurement 50 to the measurement light.

The detection light LS is then irradiated to second wavelength conversion element 164 together with the reference light LR, which carries the phase of the pair of light beams LP (S108). Due to wavelength conversion function of a non-linear optical phenomenon in the second wavelength conversion element 164, the intensity of the reference light LR is modulated to have intensity representing the intensity or phase difference of the detection light LS at each point under illumination of the object for measurement 50. The modulation depth of the intensity of the reference light LR depends also on whether the wavenumbers of the detection light LS and the reference light LR satisfies an appropriate phase matching condition, such as collinear phase matching condition in the media of the second wavelength conversion element 164. The reference light having modulated intensity by the second wavelength conversion element 164 is called modulated reference light LD. The modulated reference light LD is then impinges on the sensor array 168 and its intensity is determined (S110). Throughout this detection plural local intensities in the modulated reference light LD are measured in parallel by separate sensors in the sensor array 168. Then signal indicating each intensity value is read out from the sensor array 168 (S112).

1-1-3. Other Optical Elements

Other optical elements indicated in FIG. 1 are positioned into a suitable arrangement for the phenomenon described above. In the case when the reference light LR is a pair of light beams after exiting the first wavelength conversion element 126, a mirror 142 and a dielectric multi-layered mirror 144 are used as in FIG. 1. Specifically, the mirror 142 is arranged to relay the reference light LR from the first wavelength conversion element 126 to the second wavelength conversion element 164. The dielectric multi-layered mirror 144 is arranged to relay the detection light LS to the second wavelength conversion element 164 while light axes of the reference light LR and the detection light LS are aligned with each other. In addition to whether such mirrors are used or not, their reflection/transmission characteristics as well as their arrangement when they are used are arbitrarily determined for the actual light path arrangement according to wavelengths selected for the reference light LR, measurement light LM, and detection light LS. Similarly, the detection light cut filter 166 may be arranged. The characteristics of the detection light cut filter 166 are adjusted while considering intensity of the detection light LS leaked after transmission there and the influence of the detection light on the sensor array 168, in such a manner that the characteristics matches the wavelength of the modulated reference light LD and that of the detection light LS. For instance, when the sensor array 168 is insensible to the detection light LS then there is no need to provide the detection light cut filter 166.

Furthermore, it may be useful to adopt other optical elements or other optical path arrangement than those indicated in FIG. 1, owing to circumstances. In the case when the detection light LS is visible light or infrared light, it would be possible to use arbitrary optical elements usually used with visible light or infrared light. Even when the detection light LS is terahertz wave, it is possible to adjust convergence of the detection light to the object for measurement 50 by use of a parabolic mirror, or by use of a refraction element (prism, lens, or the like) made of cycloolefin system material that shows good transmittance at such terahertz waves, which has been developed by a part of the inventors (Patent Document 4). In addition, the reference light LR may be selected from different ones as long as it carries the phase of the pair of light beams LP. For example, it is possible to split a part of the pair of light beams LP before it impinges on the first wavelength conversion element 126 and then the part is irradiated to second wavelength conversion element 164 for the reference light LR by some arbitral optical element, not shown, without irradiating on any non-linear optical element.

1-1-4. Imaging Volume

It is possible to obtain a tomogram of the object for measurement 50 when the optical response measuring method mentioned above is reduced into practice by the optical response measuring device 100 with the structure mentioned above and the intensity information detected by the sensor array 168 is properly processed. Such imaging can be carried out over a volume range where the detection light LS is obtained without losing coherence to the measurement light LM out of a volume range that is bounded by the illumination area S irradiated by the measurement light LM and maximum depth of the reach of the measurement light LM. If the sensor array 168 is selected to one that is capable of obtaining optical intensities at different position in parallel, such as one-dimensional or two-dimensional sensor arrays, then it is possible to obtain intensity and phase values at different points under illumination in the illumination area S of the object for measurement 50 without resorting to scanning operation.

The imaging volume range will be described in relation to the optical response measuring device 100 in FIG. 1, which is an example adopting a flip configuration between the measurement light LM and the detection light LS. The range where the tomogram can be obtained from the object for measurement 50 in the object for measurement 50 is bounded by the illumination area S for lateral directions of beam, whereas its depth is determined by a range where the detection light LS is not attenuated and its coherence is not lost and where the detection light LS is not attenuated and its coherence is not lost. Specifically, intensity of the measurement light LM at each point under illumination is mainly influenced by degree of direction reversing property, such as reflection or scattering. In contrast, the phase difference of the measurement light LM at each point under illumination is mainly influenced by position of a feature under measurement F related to that phenomenon along the depth direction in the object for measurement 50. In order for such feature under measurement F to be detected, it is necessary that coherence of original detection light LS remains in the detection light LS such that the remaining coherence may have influence on the intensity of reference light LR in the second wavelength conversion element 164. Therefore, even if intensity of the detection light LS is sufficient to be detected at a position, it does not always mean that imaging is possible at that position.

1-1-5. Mechanism of Data Acquisition

In the following details of measurement mechanism will be described. We continue to rely upon the difference frequency generation (DFG) for describing the mechanism. In the first place, we focus on a phenomenon in the second wavelength conversion element 164. The second wavelength conversion element 164 receives input light of detection light LS and reference light LR (FIG. 1). The reference light LR here is a part of the pair of light beams LP. FIG. 1 depicts utilized reference light LR as transmitted fraction of the pair of light beams that were not converted to the measurement light LM in the first wavelength conversion element 126. In typical operation, the detection light LS and reference light LR are aligned with each other to have an identical optical axis such that they enter into the second wavelength conversion element 164 from the same direction, and a breadth of the reference light LR cross section is adjusted to cover the entire breadth of the cross section of the detection light LS, though the breadths are not shown in the figures.

1-1-5-1. Second Wavelength Conversion Element and Phase Matching Condition

The relationship between the second wavelength conversion element 164 and wavelengths for the reference light LR and the detection light LS is typically a collinear phase matching conditions. In this case, each intensity measured by the sensor array 168 is obtained independently, i.e., without affecting with each other, where each intensity is attributable to the detection light LS from each point under illumination included in the illumination area S of the object for measurement 50. This will be further described by way of FIG. 3.

Figure 3:
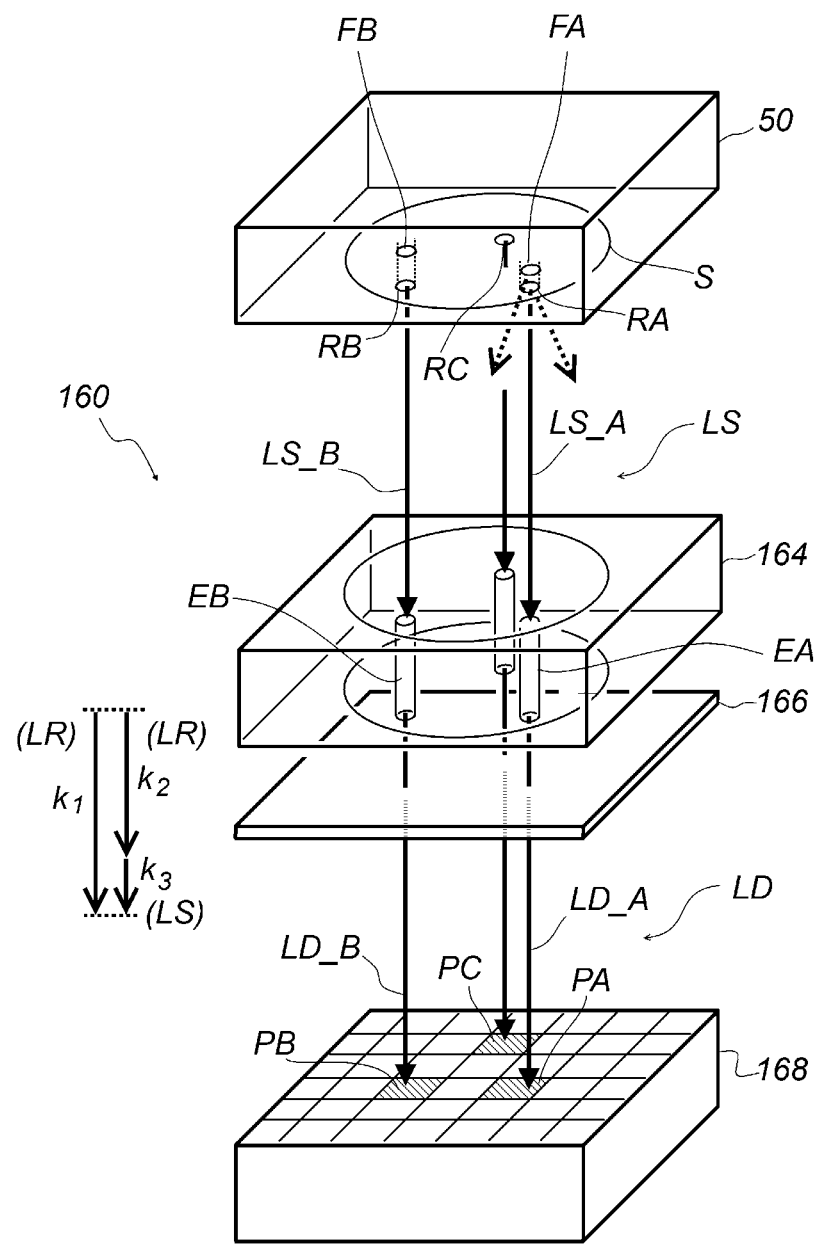
FIG. 3 is a schematic diagram illustrating a structure of reception optics in the optical response measuring device in an embodiment of the present invention.

FIG. 3 is a schematic diagram illustrating a structure of detection optics 160 in the optical response measuring device 100 depicted in FIG. 1. This example assumes that the sensor array 168 has an array of optical intensity sensors in two-dimensional manner. In addition, for explanation purposes, depicted position of the object for measurement 50 is moved to a position that is geometrically equivalent to an original position along a reflected optical path by the dielectric multi-layered mirror 144 (FIG. 1). The illumination area S of the object for measurement 50 has a two-dimensional range that matches to the breadth of the measurement light LM. Three-dimensional points within the reach of the transmitted measurement light LM at each point under illumination produce optical response according to interaction between the measurement light LM and media at the points. FIG. 3 indicates a situation in which the detection light LS from the measurement light LM at first, second, and third points under illumination RA, RB, and RC in an object for measurement 50 is detected, where these points under illumination are examples of each point under illumination in the illumination area S. The detection light is obtained from points along invasive direction at each of the first, second, and third points under illumination RA, RB, and RC. For example, since minute fractions FA and FB correspond to the feature under measurement F (not shown in FIG. 3) at the first and second points under illumination RA and RB, the detection light from the first and second points under illumination RA and RB is influenced by optical responses at minute fractions FA and FB.

Since relevant optical response at each point in an object for measurement 50 is any sort of optical responses to the measurement light LM, electromagnetic wave of the detection light LS is emitted toward various directions while its wavelength is identical to that of the measurement light LM. Thus, the detection light LS from the first point under illumination RA, for example, will travel toward various directions as illustrated in FIG. 3. Consequently, position and incidence direction of the detection light LS illuminated to the second wavelength conversion element 164 are distributed. For example, the detection light LS from the first point under illumination RA in FIG. 3 may be transmitted through the second wavelength conversion element 164 along various directions allowed by the geometrical configuration of the object for measurement 50 and the second wavelength conversion element 164.

In the second wavelength conversion element 164, since wavelength conversion is invoked by the reference light LR and detection light LS, the intensity of the reference light LR is modulated due to influence by the detection light LS at each point in the second wavelength conversion element 164 according to the local intensity and phase of the detection light LS. It should be noted that an efficient modulation of the intensity requires an appropriate phase matching condition to be satisfied in the second wavelength conversion element 164. In a typical case when a collinear phase matching is required, although the detection light LS may travel along various directions, only the detection light that travel along a direction satisfying the collinear phase matching condition has influence on the reference light LR. When the reference light LR incident on the second wavelength conversion element 164 is a collimated light beam, which is not shown in FIG. 3, then the modulated reference light LD that satisfies the collinear phase matching condition will be obtained only from areas EA and EB in the second wavelength conversion element 164 for the detection light LS corresponding respectively to the first and second points under illumination RA and RB. FIG. 3 also depicts a relationship among wavenumber vectors $k_1$, $k_2$, and $k_3$ to be satisfied in media of the second wavelength conversion element 164 by the light of first and the second wavelengths in the reference light LR and the detection light LS according to the collinear phase matching condition. That is, light beams LS_A and LS_B, which are light beams of the detection light LS from the first and second points under illumination RA and RB respectively, independently modulate local intensities of the reference light LR at areas EA and EB. Thus, resulting modulated reference light LD has modulated local intensities while it is influenced by phase information at each point under illumination. FIG. 3 indicates the modulated reference light beams LD_A and LD_B while distinguishing the modulated reference light LD for the first and second points under illumination from each other. As stated above, the modulated reference light LD whose intensity is modulated reaches toward separate sensor pixels PA and PB that corresponds to the first and second points under illumination RA and RB respectively. The detection light LS toward a direction that does not satisfy the phase matching condition with the reference light LR goes through the second wavelength conversion element 164 without interacting with each other. Phase variation at the third point under illumination RC also influences the intensity measured at the sensor pixel PC in the same manner.

This shows that the function of the second wavelength conversion element 164 is not only to convert wavelength but to conduct projection for mapping each point under illumination in the illumination area of the object for measurement 50 onto each sensor pixels of the sensor array 168. As a result of this function, the modulation is carried out according to intensity and phase at first and second points under illumination RA and RB, and such measurement is carried out concurrently. Local intensities from different points under illumination in the modulated reference light LD are not mixed up on the sensor array 168.

In a preferable structure of the present embodiment, or in a preferable structure that requires collinear phase matching condition for an effective modulation of the reference light LR in accordance with the phase of the detection light LS, a secondary effect can be expected. The detection light LS that impinges on the second wavelength conversion element 164 may have a fraction that shows less coherence or no coherence at all while having the wavelength of the detection light LS. Since most significant factor that reduces the coherence is scattering in the object for measurement 50, it is likely that the phase information for detection light travelling along a different direction from one for the mapping stated above might have been lost. Under the collinear phase matching condition it is possible to choose a direction for which the intensity modulation is performed, that is a direction for which the mapping is performed, from a range of detection light LS, by utilizing directions of the second wavelength conversion element 164 and the reference light LR. This allows us to remove detection light LS that has already lost the phase information in the measurement result.

1-1-5-2. Intensity Modulation to Reference Light

Figure 4:
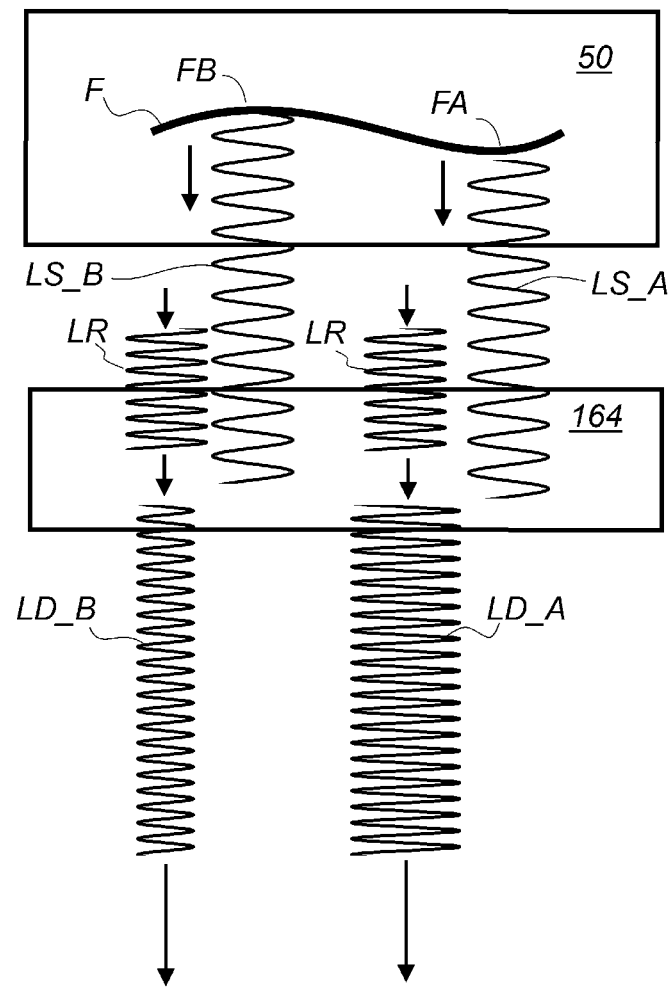
FIG. 4 is a schematic diagram illustrating the function of the second wavelength conversion element that receives reference light and detection light.

Next, the modulated reference light LD, which is a target of the intensity measurement, will be described. FIG. 4 is a schematic diagram illustrating function of the second wavelength conversion element 164 that receives reference light LR and detection light LS. When the detection light LS and the reference light LR that keep the optical responses in the first and the second points under illumination RA and RB are incident into the second wavelength conversion element 164 and the phase matching condition in the media there is satisfied, non-linear wave conversion takes place in the second wavelength conversion element 164. The degree of the non-linear wavelength conversion function at this stage is related to the optical electric field and the phase in the detection light LS.

The measurement light entering into the object for measurement 50 (not shown in FIG. 4) experiences optical response by the feature under measurement F where the degree of the response depends on position along the depth direction at each point under illumination of the object for measurement 50, the detection light LS influenced by the intensity and phase is then incident into second wavelength conversion element 164. The second wavelength conversion element 164 also receives reference light LR at the same time. Although the reference light LR is depicted in isolated waves at each position in FIG. 4, it is actually a beam, such as plane wave, and carries the phase of the pair of light beams LP, such as a part of the pair of light beams LP of the first and the second wavelengths. The detection light LS has different amplitude in the optical electric field and different phase in general depending on difference of points under illumination of the feature under measurement F. The amplitude of the optical electric field is typically influenced by differences in optical property of the feature under measurement F from the surrounding material. The differences in the optical property are those that determine a refraction index or a dielectric coefficient in a phenomenological context, such as difference of electron density. In addition, other factors that weaken electric field caused by the media in the way at the wavelength of the measurement light or detection light, such as absorption and scattering, may have such effects. On the other hand, the phase is influenced by an amount of step of refractive index found by the difference from the surrounding media. Such step of the index is basically unchanged so long as the magnitude of index of the feature under measurement F is kept with relative to the surrounding. The difference explained in terms of optical phenomenon may also be explained in a microscopic context by whether phase retardation in microscopic optical response of the feature under measurement F to the measurement light has larger value than the surrounding or not. Another factor having influence on the phase difference is optical path difference among the points under illumination in the feature under measurement F, or difference in the optical path lengths. In the case the configuration is reflective one as in FIG. 1, the optical path length is measured in a round trip path of the measurement light, which travels to the feature under measurement F and returns back from there until it exits to the outside. Actual phase difference is influenced by sum of the phase retardation mentioned above and the phase difference due to the optical path difference.

FIG. 4 illustrates a case where only the phase is different due to the optical path difference. That is, FIG. 4 is made on the assumption that the measurement light (not shown in FIG. 4) enters into the object for measurement 50 while maintaining its phase with relative to the pair of light beams (not shown in FIG. 4) and reaches the first and the second points under illumination RA and RB while maintaining the intensity, i.e., the amplitude of the optical electric field. Even in such a case, the optical path lengths for reaching the points under illumination RA and RB are different with each other as is indicated in FIG. 4. The phase difference between the reaches to the points under illumination RA and RB is, for example, 90-degree delay for the point under illumination RB with relative to the point under illumination RA when entering, and another 90-degree delay when exiting. FIG. 4 depicts an optical path difference after exiting in the detection light that corresponds to a phase difference of 180 degrees.

As explained above, the light beams LS_A and LS_B, which are detection light LS from the first and the second points under illumination RA and RB respectively, are influenced by the optical response and the phase difference corresponding to their position at the minute fractions FA and FB in the feature under measurement F. Consequently, there should found a difference in function of the non-linear wavelength conversion by the reference light LR between the light beam LS_A and the light beam LS_B, where their phase values should be determined at the first and second point under illumination RA and RB respectively. FIG. 4 illustrates a situation where the intensity of the modulated reference light LD is increased in response to the light beam LS_A from the first point under illumination RA to be modulated reference light beam LD_A, and is decreased in response to the light beam LS_B from the second point under illumination RB to be modulated reference light beam LD_B. Thus, the function of the non-linear wavelength conversion in the second wavelength conversion element 164 is sensitive to phase of the detection light LS with relative to one for the reference light LR, thus it is possible to obtain the modulated reference light beams LD_A and LD_B having intensity values corresponding to their phase values from the light beams LS_A and LS_B of the first and the second points under illumination RA and RB. Since the optical path difference between reaches to the minute fractions FA and FB on feature under measurement corresponding to the first and the second points under illumination RA and RB in the feature under measurement F influence the detection light LS, intensity values for each position of the modulated reference light LD measured by the sensor array 168 are influenced by the positions of the first and the second points FA and FB. It is to be noted that the intensity of the modulated reference light LD is also influenced when there is difference in the intensity values (difference in amplitudes of the optical electric fields) of the detection light beams LS_A and LS_B.

Figure 5:
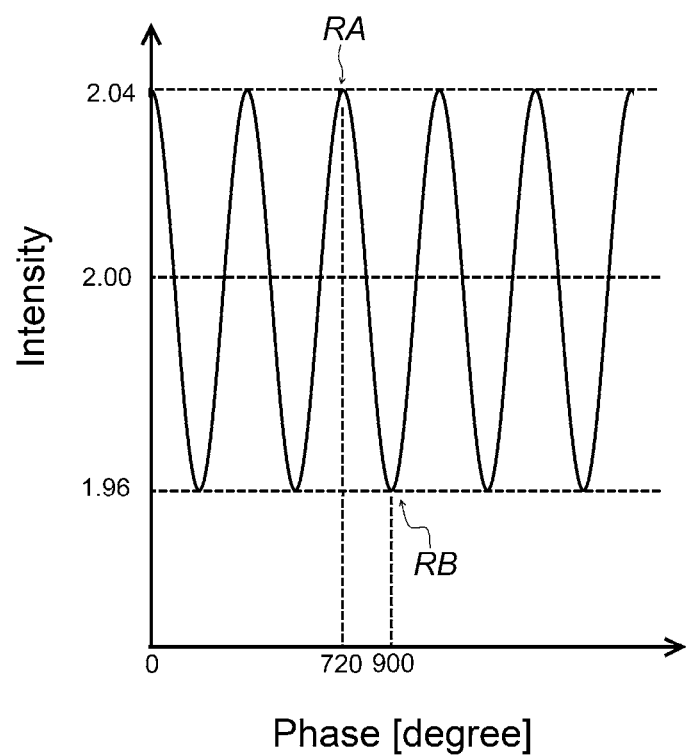
FIG. 5 is a graph showing an example intensity of modulated reference light calculated for phase values of detection light.

FIG. 5 is a graph showing an example intensity of modulated reference light calculated for phase values of detection light in an idealized optical response measurement of the present embodiment. Conditions for the calculation are the beams of reference light LR carrying the phase of a pair of light beams of the first and the second wavelengths have the same intensity, or unit value of 1, and the detection light having matched phase with the reference light LR of an intensity of 0.01 is irradiated thereto. Any phenomena that may diminish intensity or dissipate the information, such as absorption inside the object for measurement 50 or de-coherence therein, are not included in this calculation. The phase difference on the horizontal axis is determined by selecting a value of phase fixed to those of the pair of light beams LP (reference light LR) and deriving the difference with it, in units of degree. The vertical axis represents an intensity value, or power, of the modulated reference light LD detected in the sensor array 168. Other assumptions such as equal sensitivity of the sensor array 168 for the first and the second wavelengths related to the reference light LR, and zero sensitivity on direct measurement of detection light LS are made. The zero sensitivity to the detection light can be easily realized by adopting a sensor array 168 having no sensing capability of the detection light or by providing a detection light cut filter 166 (FIG. 1) when the sensor array 168 shows a sensitivity.

As shown in FIG. 5, variation of sinusoidal oscillation is observed in the sum of intensity values for the modulated reference light LD of the two wavelengths by the sensor array 168. The amplitude of the oscillation is influenced by intensity of the measurement light. That is, if the measurement light LS is not generated, or with zero intensity, then the result should be a straight line of a constant along the vertical axis, without oscillating by the phase difference. As the detection light LS increases from such situation, the sinusoidal oscillation along the phase (horizontal axis) is begin to be observed gradually. FIG. 5 shows the difference in the phase in such a manner that they correspond to positions of the minute fractions FA and FB of a feature under measurement F, a typical one in FIG. 4. As indicated in FIG. 5, when the phase difference in the detection light is attributed to the difference in position between the first and second points under illumination RA and RB, light from the first point under illumination RA increases the modulated reference light LD, whereas light from the second point under illumination RB decreases the modulated reference light LD. This is indicated in consonance with the depiction in FIG. 4.

1-1-5-3. First Wavelength Conversion Element

In order to realize such wavelength conversion as in the second wavelength conversion element 164, a certain relationship should be realized between the detection light LS and reference light LR, or between the measurement light irradiated to the object for measurement 50 for obtaining the detection light and a pair of light beams for the reference light LR. This will be explained by referring again to FIG. 1. The first wavelength conversion element 126 produces the measurement light LM from the pair of light beams LP of the first and the second wavelengths by difference frequency generation. During this process, the phase in generated the measurement light LM is determined by phase values of light of the first and the second wavelengths. To be more specific, the phase of the measurement light LM keeps a certain relationship with the phase of the first wavelength, and it keeps another certain relationship with the phase of the second wavelength. To keep a certain relationship here means that continuous and linear relationship is found in two optical waves, where one makes oscillation for a phase amount for a period of time and the other makes oscillation for another phase amount for the same period of time. In such definition, it is allowed that the measurement light and the light of the first wavelength keep a certain relationship when the measurement light and the light of the second wavelength keep another certain relationship at a time.

It is to be noted that temporal variation of relative phases between light of the first wavelength and light of the second wavelength may be kept constant or changed. This is because, although the pair of light beams LP formed by light of the first and the second wavelengths is used for generating the measurement light LM, exactly the same part of them or light carrying the same phase of them will become the reference light LR for the detection light LS. That is, to speak plainly, the measurement light LM keeps its coherent with phase of beats between light of the first wavelength and light of the second wavelength. Thus, assuming that the phase relationship between the light of the first wavelength and light of the second wavelength varies due to unknown reason, phases of the measurement light LM and the detection light LS are generated instantly in accordance with the variation. As a result, such temporal variation has no effect on the function in the second wavelength conversion element 164, thus the resulting intensity measurement of the modulated reference light LD is not affected at all.

1-2. When OPG (Optical Parametric Generation) Adopted

It is possible to realize operation similar to that mentioned above by adopting OPG (Optical parametric generation), a non-linear optical phenomenon of different type from the DFG. Since the structure or operation of an embodiment using OPG can be similarly explained in FIGS. 1-5, we will explain mainly different part from those in Section 1-1 here.

Light source in the embodiment of OPG is a laser having a single wavelength (first wavelength) and the light (referenced by LP) is input as a pump light to first wavelength conversion element 126. The first wavelength conversion element 126 is selected to be made of material that generates beams of light of two wavelengths by optical parametric generation from the pump light. The beams of light generated by the first wavelength conversion element 126 though the optical parametric generation has two wavelengths and are referred to as a signal light and an idler light. The signal light of these beams of light is used for the measurement light LM (FIG. 1), and the idler light is used for the reference light LR together with a part of the pump light. The wavelengths of the measurement light LM and the idler light are determined by the OPG operation in the first wavelength conversion element 126 from a view point of the governing laws, and selected to be a wavelength suitable for measurement by the measurement light LM, or a measurement wavelength, from a view point of the application.

The second wavelength conversion element 164 generates modulated reference light LD based on a reverse function of one in the first wavelength conversion element 126. For this purpose, the second wavelength conversion element 164 is irradiated by detection light LS obtained from an illumination area on the object for measurement irradiated by the measurement light LM and a reference light LR. Non-linear optical phenomenon occurred in the second wavelength conversion element 164 is sum frequency generation of a part of the reference light LR and the detection light LS, which were the idler light and the signal light in the first wavelength conversion element 126. The reference light LR carries a phase of the pump light and the idler light in the first wavelength conversion element 126. The detection light LS has the same wavelength as the measurement light LM and is influenced by the phase information in the object for measurement 50. Thus the second wavelength conversion element 164 is operated on light beams LS_A and LS_B, which are detection light LS from the first and second points under illumination RA and RB respectively and modulates local intensities of reference light LR independently, as was described in the above with reference to FIGS. 3 and 4. Consequently, partial intensities of the modulated reference light LD are modulated such that they are influenced by the phase information at each point under illumination. Collinear phase matching condition in the second wavelength conversion element 164 and resulting projection operation are the same as those in FIG. 3. Intensity of the light of an identical wavelength to the pump light (light of first wavelength) in the modulated reference light LD is measured by the sensor array 168. Since light beams LS_A and LS_B of the detection light LS are superimposed, or interfered, to pump light (light of first wavelength) and signal light (light of second wavelength) in the reference light LR during the non-linear wavelength conversion (sum frequency generation) in the second wavelength conversion element 164, the intensity of the modulated reference light LD is influenced by the phase information of the object for measurement 50. The mechanism described here is the same as those described in connection with DFG with reference to FIG. 4. Also, the operation of intensity measurement of the modulated reference light LD by the sensor array 168 is the same as explained. In this case, the detection light cut filter 166 is configured such that it can pass light over the wavelength range of pump light in the reference light LR, for example. In addition, the calculated example for the intensity of the modulated reference light LD against phase of the detection light LS in FIG. 5 is also the same. Moreover, the optical response measuring method can be practiced similarly in the operation step S102 of the light source 122, except that the pump light LP is generated instead of the pair of light beams.

1-3. Similar Examples to DFG and OPG

DFG and OPG mentioned above are typical examples of phenomena that can be applied to the present embodiment, thus any of non-linear optical phenomena similar to those can be applied to embodiment of the present invention. An example applicable to the embodiment of the present invention is a phenomenon called injection seeded OPG, a type of OPG. Since light of two wavelengths is input to the first wavelength conversion element 126 in this injection seeded OPG, its operation is similar to a case of DFG (difference frequency generation). It should be noted that another example applicable to the embodiment of the present invention is a phenomenon called optical parametric amplification (OPA). The term OPA is one that denotes the same operation as the DFG mentioned above while paying attention on light of third wavelength. The term OPA is used in cases when the phenomenon is recognized as one that amplifies second wavelength light, which is a longer wavelength than first wavelength. The phenomenon called the optical parametric amplification (OPA) can be explained in the same way as those for the DFG stated above.

1-4. OPG (Optical Parametric Generation)

Figure 6:
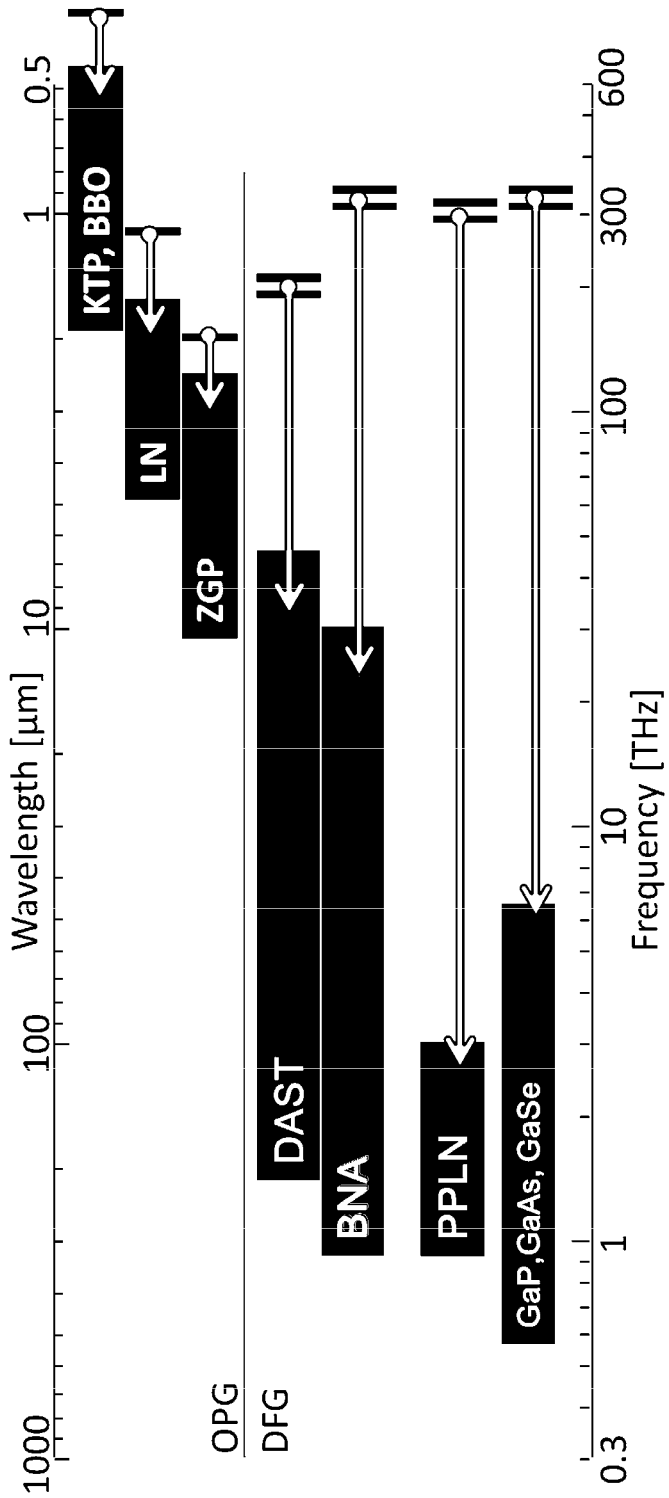
FIG. 6 is an explanation chart indicating representative combinations of wavelengths for pair of light beams and non-linear optical crystals, and wavelength ranges (frequency ranges) of measurement light generated from each combination.

Schemes described in the embodiment of the present invention can be practiced in principle if the operation of the second wavelength conversion element 164 is realized, and necessary measurement light is generated by the first wavelength conversion element 126 for this purpose. FIG. 6 is an explanation chart indicating representative combinations of wavelengths for pair of light beams and non-linear optical crystals and wavelength ranges, or frequency ranges, of measurement light generated from each combination. The relationship indicated in FIG. 6 would be summarized as in Table 1 with numerical values for the first and the second wavelengths for the pair of light beams for each material.

TABLE 1

| 1st Wavelength Conversion Element | 1st, 2nd Wavelength | Frequency or Wavelength of Measurement Light | Non-linear Optical Phenomenon |
|---|---|---|---|
| DAST | 1.3 µm-1.7 µm | 1 THz-40 THz | DFG |
| BNA | 0.8 µm-1.3 µm | 1 THz-30 THz | DFG |
| PPLN | 0.8 µm-1.5 µm | 1 THz-3 THz | DFG |
| GaP | 0.9 µm-1.1 µm | 0.3 THz-4.5 THz | DFG |
| GaSe | 1.0 µm-1.1 µm | 0.1 THz-2 THz | DFG |
| ZGP | 2 µm-3 µm | 4 µm-12 µm | OPG |
| LN | 1064 nm | 1.3 µm-5 µm | OPG |
| KTP | 532 nm | 0.6 µm-4 µm | OPG |
| BBO | 355 nm | 0.4 µm-3 µm | OPG |

NOTE:
DAST: 4-dimethylamino-N-methyl-4-stilbazolium tosylate,
BNA: N-Benzyl-2-methyl-4-nitroaniline,
PPLN: Periodically Poled Lithium Niobate ($LiNbO_3$),
ZGP: $ZnGeP_2$,
LN: $LiNbO_3$,
BBO: $\beta$-$BaB_2O_4$,
KTP: $KTiOPO_4$,
DFG: Difference Frequency Generation,
OPG: Optical Parametric Generation The same combinations for the wavelength and material as those for the first wavelength conversion element 126 may be adopted for the second wavelength conversion element 164.

For example, when such organic non-linear crystal as DAST or BNA is adopted for the first wavelength conversion element 126 and the second wavelength conversion element 164, the value for $\chi^{(2)}$(tensor element) will be 10 times or more for inorganic crystals. This means that the non-linear optical phenomenon can be easily seen for measuring wavelength of THz range, therefore, there is no difficulty in practicing the embodiment in such a range.

The measurement light LM irradiated to the object for measurement 50 may be infrared light or terahertz light as indicated in Table 1. The wavelength is chosen from available wavelength range based on type of the object for measurement 50, type of tissue in the object for measurement 50 (feature under measurement F) is to be detected, and property of the optical response. Generally speaking, longer wavelength will be chosen in order to obtain structural information of deep invasion from the surface because a longer wavelength will have more significant transmission capability.

In actual optical response measuring device 100, first wavelength conversion element 126 and second wavelength conversion element 164 can be of the same material, or of different material. Typically, it is favorable that the same material is adopted for the first wavelength conversion element 126 and the second wavelength conversion element 164. In the case DFG is adopted, for example, if the pair of light beams of the first and the second wavelengths is adopted and made incident on a first wavelength conversion element 126 of DAST crystal, and the measurement light maintaining the phase with relative to the pair of light beams, the it is preferable that DAST is also selected for the second wavelength conversion element 164 on which reference light and detection light are irradiated. This is because the first wavelength conversion element 126 and the second wavelength conversion element 164 can meet a phase matching condition at the same wavelength when the measurement wavelength light is modulated for the measurement. In the case OPG is adopted, it is also preferable that the same material is adopted for the first wavelength conversion element 126 and the second wavelength conversion element 164 based on the same reason.

1-5. Summary of the Section

In the embodiment of the present invention, measurement is carried out on the shape and position of a feature under measurement F in the object for measurement 50. The phase values of the detection light LS obtained at the first and second points under illumination RA and RB in the illumination area S of the object for measurement 50, or the first phase and the second phase, are influenced especially by internal local structure along the invasive direction inside the object for measurement 50, such as the feature under measurement F of the object for measurement 50 at each position. Therefore, if the sensor array 168 is used for the measurement, the first and second intensities in the modulated reference light LD that are influenced by the first and the second phase values enable to make a measurement of minute fractions FA and FB in a feature under measurement F inside of the object for measurement 50 without using scanning technique.

Advantages of the embodiment of the present invention may be found in the fact that detection wavelength of detectors and wavelength for measurement or detection are separated from each other. Even if the measurement is attempted with measurement or detection light of a wavelength for which manufacturing of the detectors is difficult, it is possible to fit a detector, such as a sensor array 168, to a wavelength of the modulated reference light LD. This is advantageous in that it allows us to pursue both of a wavelength in view of obtaining optical response from the object for measurement 50 and a detector such as a sensor array 168 for concurrent detecting plural points under illumination.

In addition, as is evident from the embodiment of the present invention, the structure of the optical response measuring device 100 indicated in FIG. 1 is merely an exemplary one. For example, it is not necessary to configure directions of the measurement light and detection light such that the detection light is received in a specular reflection direction of the measurement light. When the measurement light is selected to have a wavelength that can travel through the object for measurement 50, it may be advantageous to obtain optical response by light passing through, or to receive detection light that goes off from an optical axis due to scattering for obtaining optical response of the object for measurement 50 to the measurement light.

Furthermore, in cases when the reference light is a part of the pair of light beams that will generate the measurement light LM, then it is not necessary that the reference light is one that passed through the first wavelength conversion element 126 as in FIG. 1. For example, it is possible to split the pair of light beams before entering into the first wavelength conversion element 126 and redirect the split part to the second wavelength conversion element 164 by way of appropriate relay optics.

2. Capturing Tomogram

From now on, frequency sweeping technique in application for obtaining tomogram by use of the measurement scheme of optical response in the embodiment of the present invention will be described. It is advantageous to modulate a wavelength of detection light or frequency by sweeping when capturing a tomogram inside of the object for measurement 50 in the embodiment of the present invention. It is possible to capture tomogram information if the frequency sweeping is carried out in the detection light LS for obtaining tomogram information in a similar manner to SS-OCT, which has been adopted in existing OCTs. In this embodiment, it is possible to capture pieces of intensity information of detection light LS corresponding to time from the object for measurement 50, in place of the modulated reference light LD, based on measurement light LM with different wavelengths if frequency of measurement light LM is swept and irradiated. Tomogram information may be derived easily form such pieces of information by Fourier transform.

It should be noted that the measurement principle mentioned above is applicable as in the same way when the frequency sweep is adopted for the detection light. This is because it is possible to perform non-linear conversion in the first wavelength conversion element 126 and the second wavelength conversion element 164 at each frequency (each wavelength) of the detection light, there is no need for paying attention on the difference of frequency (wavelength) for the time difference for which measurement light (detection light) travels from the first wavelength conversion element 126 to the second wavelength conversion element 164, and the measurement principle is true at every moment. The wavelength of at least any of the pair of light beams of the first wavelength and the second wavelength is swept for sweeping the frequency of the detection light. FIG. 1 depicts a modulation controller 128 for frequency sweeping. The light source 122 modulates any of the first wavelength and the second wavelength in response to control by the modulation controller 128, thereby at least one of the two wavelengths of the reference light is swept. The wavelength of the detection light entering into the sensor array 168 is also swept.

Typical timing of the frequency sweeping in this embodiment of the present invention is after the signal readout (FIG. 2, S112) subsequent to the intensity detection corresponding to plural points under illumination, or during the readout concurrently. This is expressed in FIG. 2 by step S114 of updating frequency after step S122 of signal readout. Thus, there is no need to extremely boost the frequency sweep rate. Also, there is no particular trouble in the readout of the sensor array 168.

By the way, existing SS-OCT requires at least one frequency sweep action to obtain invasive direction information at a focal point, (so called A-scan) for the information along the invasive direction. This is because the frequency sweep is assigned to a process that needs most frequent repetition in the process loop for scanning the focal point. As a result, processing speed of existing SS-OCT is regulated by process time for a single A-scan, that is, capturing rate of tomograms is determined by the frequency sweep rate for the light source.

The embodiments of the present invention have been described specifically throughout the description set forth herein. Any parts of the description in this specification, including the embodiments and examples are provided for the purpose of explaining the present invention; thus the scope of the invention should be determined based on recitations of the claims. Furthermore, any other variations based on any combination in the embodiment should be considered in the present invention, which variations should be also within a scope of the present invention.

INDUSTRIAL APPLICABILITY

The present invention is applicable to any device for measuring optical response of an object for measurement.

LIST OF REFERENCE SYMBOLS 100 optical response measuring device
120 illumination optics
122 light source
124 telescope optics
126 first wavelength conversion element
128 modulation controller
142 mirror
144 dielectric multi-layered mirror
160 detection optics
164 second wavelength conversion element
166 detection light cut filter
168 sensor array
50 object for measurement
LP pair of light beams, or pump light
LR reference light
LM measurement light
LS, LS_A, LS_B detection light
LD, LD_A, LD_B modulated reference light
F feature under measurement
FA, FB minute fraction of feature under measurement
RA, RB, RC first-, second-, and third points under illumination
EA, EB areas in the second wavelength conversion element
PA, PB, PC sensor pixels
S illumination area The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An optical response measuring device comprising:
   a light source for generating a pair of light beams, a first light beam of the pair of light beams having a first wavelength and the second light beam of the pair of light beams having a second wavelength;
   a first wavelength conversion element on which the pair of light beams is made incident, first wavelength conversion element configured to generate a measurement light beam based on the first light beam and based on the second light beam;
   a second wavelength conversion element, on which a detection light beam obtained from an illumination area on an object by the measurement light beam and a reference light beam are made incident, the second wavelength conversion element configured to generate a modulated reference light beam in response to both the reference light beam and the detection light beam, wherein the reference light beam has phases that are maintained relative to the phases of the pair of light beams, wherein the detection light beam includes at least two light beams, a first detection light beam having a first phase and being obtained at a first point of illumination of the object and a second detection light beam having a second phase and being obtained at a second point of illumination of the object, the first phase and the second phase containing responses of the object at the first point and the second point respectively, and wherein the second wavelength conversion element is configured to modulate the modulated reference light beam to have a first local intensity and a second local intensity in accordance with the first phase and the second phase of the at least two beams in the detection light beam respectively; and
   a light intensity sensor array, on which the modulated reference light beams are made incident for measuring the first local intensity and the second local intensity in the modulated reference light beam, the first local intensity and the second local intensity corresponding respectively to the first phase and the second phase in the first and second light beams of the detection light beam.

2. The optical response measuring device according to claim 1,
   wherein the detection light beam and the reference light beam are made incident on the second wavelength conversion element while being aligned with each other, and
   wherein the modulated reference light beam is generated under a collinear phase matching condition.

3. The optical response measuring device according to claim 1,
   wherein the light intensity sensor array is a two-dimensional sensor array,
   wherein the illumination area on the object has a third point, the third point spanning a two-dimensional plane together with the first point and the second point,
   wherein the detection light beam further includes a detection third light beam having a third phase and is obtained at the third point, the third phase containing a response of the object at the third point,
   wherein the second wavelength conversion element is configured to modulate the modulated reference light beam to have a third local intensity in response to the third phase of the third detection light beam in the detection light beam,
   wherein the light intensity sensor array is configured to measure the third local intensity of the modulated reference light beam together with the first and the second local intensities, and
   wherein the optical response measuring device performs measurement over the object in the illumination area without conducting a scanning operation.

4. The optical response measuring device according to claim 1, further comprising:
   a modulation controller for modulating at least one of the first wavelength and the second wavelength.

5. A method of measuring an optical response comprising steps of:
   generating a pair of light beams, a first light beam of the pair of light beams having of a first wavelength and a second light beam of the pair of light beams having a second wavelength;
   obtaining a measurement light beam by making the pair of light beams incident on a first wavelength conversion element, the first wavelength conversion element configured to generate the measurement light beam based on the first light beam for illuminating an illumination area on the object;
   obtaining a detection light beam having a first phase and a second phase by illuminating the illumination area with the measurement light beam, wherein the detection light beam includes at least two light beams, a first detection light beam having a first phase and being obtained at a first point under illumination and a second detection light beam having a second phase and being obtained at a second point under illumination, and the first phase and the second phase containing responses of the object at the first point and the second point, respectively;
   obtaining a modulated reference light beam by making both a reference light beam and the detection light beam incident on a second wavelength conversion element, wherein the reference light beam has phases that are maintained with relative to the phases in the pair of light beams, and wherein the second wavelength conversion element is configured to modulate the modulated reference light beam to have a first local intensity and a second local intensity in accordance with the first phase and the second phase of the at least two beams in the detection light beam respectively; and
   measuring the first local intensity and the second local intensity in the modulated reference light beam by making the modulated reference light beam incident on a light intensity sensor array, the first local intensity and the second local intensity corresponding respectively to the first phase and the second phase in the at least two light beams in the detection light beam.

6. The optical response measuring method according to claim 5,
wherein the detection light beam and the reference light beam is made incident on the second wavelength conversion element while being aligned with each other, and
wherein the modulated reference light beam is generated under a collinear phase matching condition.

7. The optical response measuring method according to claim 5,
wherein the light intensity sensor array is a two-dimensional sensor array,
wherein the illumination area on the object has a third point under illumination, the third point spanning a two-dimensional plane together with the first and the second points,
wherein the detection light beam further has a third detection light beam having a third phase and is obtained at the third point, the third phase containing response of the object at the third point,
wherein the second wavelength conversion element is configured to modulate the modulated reference light beam to have a third local intensity in response to the third phase of the third detection light beam in the detection light beam,
wherein the third local intensity of the modulated reference light beam is measured by the light intensity sensor array together with the first and the second local intensities, and
wherein the optical response measuring device performs measurement over the object in the illumination area without conducting a scanning operation.

8. The optical response measuring method according to claim 5 further comprising a step of:
modulating at least one of the first wavelength and the second wavelength.

* * * * *